United States Patent [19]

Koniz et al.

[11] 4,231,751
[45] Nov. 4, 1980

[54] NOVEL METHOD OF TESTING A CHARGE CALCINED ALUMINA TO DETERMINE ITS SUITABILITY FOR USE IN HYDROCARBON CONVERSION

[75] Inventors: Leon F. Koniz, Poughkeepsie; John H. Estes, Wappingers Falls, both of N.Y.

[73] Assignee: Texaco Inc., White Plains, N.Y.

[21] Appl. No.: 1,235

[22] Filed: Jan. 5, 1979

Related U.S. Application Data

[60] Division of Ser. No. 887,392, Mar. 16, 1978, Pat. No. 4,171,329, which is a continuation-in-part of Ser. No. 704,003, Jul. 9, 1976, abandoned.

[51] Int. Cl.² ............... G01N 21/04; G01N 31/02
[52] U.S. Cl. ........................................... 23/230 R
[58] Field of Search ............ 23/230 R; 423/628; 252/463, 465, 466 PT; 260/672 R

[56] References Cited

U.S. PATENT DOCUMENTS

| | | | |
|---|---|---|---|
| 2,881,051 | 4/1959 | Pingard | 423/628 |
| 2,928,792 | 3/1960 | Bertolacini | 23/230 R |
| 3,249,557 | 5/1966 | Oleck | 423/628 X |
| 3,787,183 | 1/1974 | Kennedy, Jr. | 23/230 R |
| 3,846,287 | 11/1974 | Jaffe et al. | 208/216 R |

FOREIGN PATENT DOCUMENTS 963486  7/1964  United Kingdom .................. 423/628

OTHER PUBLICATIONS

Osment, "Active Aluminas as Catalyst Supports for Treatment of Automotive Exhaust Emissions"; Society of Automotive Engineers, International Automotive Engineering Congress, Detroit, Mich., Jan. 8–12, 1973.

*Primary Examiner*—Arnold Turk
*Attorney, Agent, or Firm*—Carl G. Ries; Robert A. Kulason; Carl G. Seutter

[57] ABSTRACT

Alkylaromatic charge hydrocarbons such as toluene are steam dealkylated in the presence of catalyst which typically contains oxides of nickel, chromium, and potassium on an activated high-purity alumina. It is a feature of this invention that the high-purity alumina is activated by calcining followed by addition thereto of alkaline earth metal such as calcium or magnesium. A test is disclosed according to which it may be determined which high-purity aluminas are suitable for use.

2 Claims, No Drawings

NOVEL METHOD OF TESTING A CHARGE CALCINED ALUMINA TO DETERMINE ITS SUITABILITY FOR USE IN HYDROCARBON CONVERSION

This is a division of application Ser. No. 887,392 filed Mar. 16, 1978 and now U.S. patent No. 4,171,329 which is a continuation in part of application Ser. No. 704,003 filed July 9, 1976 now abandoned.

FIELD OF THE INVENTION

This invention relates to a process for steam dealkylation. More particularly, it relates to the use of a novel catalyst system, including an activated high-purity alumina catalyst support, which permits attainment of desired levels of conversion, yield, and selectivity in hydrocarbon conversion processes, typically steam dealkylation.

BACKGROUND OF THE INVENTION

As is well known to those skilled in the art, various catalysts are used in processing. Many of these catalysts are characterized by the presence of catalytically active components on a support. Attempts are constantly being made to improve the properties of the support and to thus permit attainment of a catalyst composition, containing support preferably plus other ingredients, which is characterized by desirable properties including, for example, conversion, yield, selectivity, etc.

It is an object of this invention to provide a novel steam dealkylation process. Other objects will be apparent to those skilled in the art.

STATEMENT OF THE INVENTION

In accordance with certain of its aspects, this invention is directed to a process for dealkylating an alkylaromatic hydrocarbon charge stream which comprises:

passing a mixture of steam and alkylaromatic hydrocarbon, at steam dealkylating conditions, into contact with an activated supported catalyst containing 0.5–40 parts of $(VIII)_{2/n} O$, 0–40 parts of $(VI)_{2/m} O$, 0–5 parts of $(I)_2 O$, and 15–99.5 parts of alumina support wherein VIII is a metal, of valence n, of Group VIII of the Periodic Table, VI is a metal of Group VI B of the Periodic Table of valence m, and I is a metal of Group I A of the Periodic Table, said alumina support having been prepared by:

(i) adding to a calcined charge high-purity alumina an activating amount of at least one alkaline earth metal together with a catalytically acceptable anion;

(ii) maintaining said charge alumina in contact with said activating amount of said alkaline earth metal whereby said alkaline earth metal is distributed throughout at least a portion of the body of said charge alumina, thereby forming desired product treated alumina containing an activating amount of at least one alkaline earth metal together with at least one catalytically acceptable anion; and (iii) recovering said desired product treated alumina containing an activating amount of alkaline earth metal together with at least one catalytically acceptable anion.

DESCRIPTION OF THE INVENTION

The high-purity aluminas which may be used as charge to prepare the catalyst useful in practice of the process of this invention are typically substantially pure alumina, i.e. $Al_2O_3$. These aluminas may commonly be characterized by the fact that they contain little or no measurable content of metal impurities—the amounts present usually being measured in parts per million and commonly they are found to be less than 100 ppm. These aluminas may typically be essentially free of sulfate ion; they may contain less than 500 ppm sulfate, and frequently (depending on the particular source or mode of preparation) less than that. They are also found to contain little or no alkaline earth metal (barium, magnesium, calcium, etc.); and, when present, alkaline earth metals may be found in amounts less than, say, 300 ppm and usually below 100 ppm. More typically, the alkaline earth metal content may be 10–70 ppm.

Typical of these high-purity aluminas which may be available may be:

(i) alumina derived from chemically pure aluminum hydroxide which is obtained as by dehydration of the precipitate obtained by reaction of a soluble salt of aluminum (such as aluminum acetate) and a base (such as ammonium hydroxide);

(ii) alumina derived from chemically pure aluminum which is obtained by dissolving the aluminum in a solvent (e.g. caustic soda to form sodium aluminate) from which aluminum hydroxide is precipitated (e.g. by addition of acid), the hydroxide being dehydrated to alumina;

(iii) alumina derived by combustion of aluminum metal;

(iv) alumina found naturally occurring in pure state as a mineral;

(v) alumina recovered as by-product from chemical reactions wherein, because of the nature of the reaction or the normal recovery technique, the alumina is recovered in substantially pure form; etc.

Typical of such pure aluminas is the Catapal S-type of alumina derived as a by-product from the preparation of alcohols by a process which uses aluminum alcoholates. U.S. Pat. No. 2,892,858, for example, discloses a Ziegler synthesis of higher alcohols and the formation of such a by-product alumina.

The typical Catapal S-type alumina may contain no measurable content of alkali metal when measured as sodium by standard analytical techniques. The principal impurity normally is titanium dioxide, $TiO_2$, in amount (as $TiO_2$) of 150–700 ppm, typically 500–700 ppm, say 600 ppm. Other impurities typically include: $SiO_2$, silicon dioxide, in amount (as $SiO_2$) of 80–120 ppm, say 100 ppm; iron oxides in amount (as $Fe_2O_3$) of 27–61 ppm, say 40 ppm; alkaline earth metals in amount (as MgO) of 14–70 ppm, say 50 ppm; and alkali metals in amount (as $Na_2O$) too low to determine by the usual analytical techniques. The titanium, silicon, iron, and alkaline earth metals are present as oxides (either as such or as in complexes); and for convenience the concentration is reported as pure metal. The alumina may be substantially free of other impurities.

The high-purity alumina, like the other high-purity aluminas which may be used in practice of the process of this invention, is particularly characterized by its substantial freedom from alkaline earth metals which, if present at all, are typically present in amounts less than about 100 ppm, say 10–70 ppm, or even less.

Although the high purity of the Catapal S-type alumina, and the other aluminas obtained therefrom including Catapal S-type gamma alumina, would seem to suggest that they may be particularly useful in applications which would apparently be benefitted by this low level of impurities, in practice this is not found to be so.

If pure gamma alumina derived from a Catapal S alumina, for example, be used, e.g. in a catalyst for the steam dealkylation of hydrocarbons such as toluene, it is found that the benzene yield, benzene selectivity, etc., are substantially less than is desired—and specifically much less than may be attained by the process of this invention. The yield may be a third less and the selectivity may be a third less.

These observations are also found in the case of other high-purity aluminas which typically contain less than about 100 ppm of alkaline earth metal such as calcium; including, for example, Catapal S-type alpha alumina monohydrate, alpha alumina trihydrate, etc., which may be readily converted to gamma alumina, a preferred support for catalyst in many reactions.

It has unexpectedly been found, if one uses a high-purity alumina as a basis for preparing a catalyst support, that the results are found to be unsatisfactory. Alternatively expressed, it has been found that if one uses prior art high-quality alumina, the results are found to be erratic to unsatisfactory.

It has been unexpectedly found that the reason these high-purity aluminas do not function effectively in many catalytic processes is because they are "too pure", i.e. they contain alkaline earth metal in amount less than about 100 ppm; and it is now found that presence of an activating amount of alkaline earth metal is usually necessary (and at the very least helpful) in attaining maximum activity of catalysts prepared from so-called pure aluminas.

In practice of the process of this invention according to certain of its aspects, an alkaline earth metal is added to the high-purity alumina. It may be possible to add the activating amount of alkaline earth metal to the high-purity alumina support at any time during preparation of the catalyst after the alumina has been calcined and prior to addition of catalytic components such as metals.

It is unexpectedly found that (contrary to prior art, q.v. U.S. Pat. No. 3,846,287, for example, relating to hydrodesulfurization) the addition of, e.g. calcium, to such a precalcined alumina gives outstanding results in, e.g. steam demethylation; in contrast, the addition of, e.g. calcium, in the activating amounts hereinafter noted, to a high-purity alumina, followed by calcination after addition, does not permit attainment of the desired results.

It will be appreciated that during preparation of a catalyst composition from alumina, the alumina charge may be precalcined, then various metals such as nickel, etc. may be added, followed by second and optionally subsequent calcinations after addition of various components. The addition of alkaline earth metals in practice of this invention is made after (but not prior to) the precalcination of the charge alumina. Although it may be made subsequent to further addition of other components (followed in each case by calcination), it is preferably made prior to this point; i.e. addition of alkaline earth metal is preferably made immediately after the high-purity charge alumina is precalcined and prior to further treatment.

Although the alkaline earth metal may be a metal of Group II A of the Periodic Table, it is preferably barium, magnesium, strontium, or calcium. In the preferred embodiment, it is calcium.

In practice of this invention, there may be added to the calcined charge alumina an activating amount of alkaline earth metal together with at least one catalytically acceptable anion. Although the alkaline earth metal may be added, for example, to an alpha alumina monohydrate Catapal S or to any of the aluminas to which it may be converted during processing, it is preferred to add the alkaline earth metal to the Catapal S-derived (otherwise pure except for its content of titanium dioxide) gamma alumina.

An activating amount of alkaline earth metal is commonly about 0.01–0.5% of the support, more preferably 0.1–0.25%, say about 0.2% of the support. Since a typical catalyst contains other components (e.g. metals, etc.), this may be correspond to about 0.005–0.25%, more preferably 0.05–0.10%, say about 0.1% of the total catalyst containing support plus metals, etc.

Amounts of alkaline earth metal in excess of the noted maximum (5000 ppm or 0.5%) tend to give decreased yields, while amounts below the noted minimum (100 ppm or 0.01%) tend to give both decreased yield and selectivity during, e.g. steam dealkylation of toluene.

The alkaline earth metal is present together with a catalytically acceptable anion. Catalytically acceptable anions may include any anions which are found with alkaline earth metal compounds which do not produce a detrimental or undesirable effect on the catalyst system. Catalytically acceptable anions may include those which appear to be inert, or those which moderate the catalytic activity, or those which possess desirable independent catalytic activity, or those which augment to promote the desired catalytic activity.

It will be apparent to those skilled in the art that the nature of the catalytically acceptable anion will be dependent on the ultimate catalytic process in which the catalyst is to be used. Common catalytically acceptable anions include (i) oxide (as in calcium oxide); (ii) hydroxide (as in calcium hydroxide, etc.); (iii) carbonate (as in calcium carbonate, etc.); (iv) organic anions which are volatilizable or decomposable (as in calcium acetate, magnesium formate, barium propionate, etc.).

The preferred anions are acetate, oxide, hydroxide, and carbonate; and preferred compounds by which alkaline earth metal may be added include calcium acetate, calcium oxide, calcium hydroxide, magnesium carbonate, calcium sulfate, calcium carbonate, barium acetate, etc.

The alkaline earth metal, preferably calcium, may be added to the high-purity calcined charge alumina by the following processes:

(i) immersing the calcined high-purity charge alumina in a solution of a soluble alkaline earth metal composition (e.g. aqueous solution of calcium acetate), letting it stand, drying, calcining, and repeating the procedure;

(ii) immersing the calcined high-purity charge alumina in a suspension of insoluble or slightly soluble alkaline earth metal compound (e.g. aqueous suspension of calcium oxide, calcium hydroxide, calcium carbonate, magnesium carbonate, etc.) letting it stand, drying, calcining, and repeating the procedure;

(iii) physically blending, as by tumbling, the charge high-purity calcined alumina with finely divided, e.g. calcium oxide, magnesium carbonate, calcium carbonate, etc., optionally in the presence of steam or aqueous spray; etc.

The various techniques for introducing alkaline earth metal into the charge calcined high-purity alumina typically permit attainment of a product in which the alkaline earth metal (in activating amount) is distributed throughout at least a portion of the body, e.g. over the outside of the charge calcined alumina. When the addition technique includes contact with a solution, the distribution may be substantially uniform over the entire outside surface. When the addition technique includes contact with a solid as by tumbling, the distribution may be uniform but less complete over the entire surface.

In the preferred embodiment, the distribution of added alkaline earth metal, preferably calcium, is substantially uniform over the outside of the charge precalcined alumina; and it is also found distributed throughout at least a portion (and more preferably throughout the entire body) of the charge precalcined high-purity alumina.

It is possible to introduce the desired alkaline earth metal (i) into an alpha alumina trihydrate before, during or after its conversion to the alpha alumina monohydrate; (ii) into an alpha alumina monohydrate prior to, during or after its conversion to gamma alumina; (iii) into a gamma alumina prior to, during or after further treatment; etc. Specifically, it may be possible to introduce alkaline earth metal (i) after the final catalyst composition including alumina plus metals is formulated; (ii) prior to, concurrently with or immediately after addition of any one of the catalyst component metals; (iii) before or after any of the drying or calcination steps. The only requirement is that the composition to which the alkaline earth metal is introduced shall have already been calcined at least once.

It is, however, preferred that the activating amount of alkaline earth metal and catalytically acceptable anion be added to the calcined charge high-purity gamma alumina prior to addition thereto of the other components of the finished catalyst composition. Preferably, the so-obtained gamma alumina contains an activating amount of alkaline earth metal distributed over the outside of the alumina and over at least a portion of and, more preferably, throughout substantially the entire body of the alumina.

The high-purity alumina which may be used to prepare the catalyst of this invention is typically a gamma alumina in the form of an extrudate of 1.5 mm diameter and 1.5 mm length.

The gamma alumina is then calcined for 1–5 hours, say 2 hours, at 900° F.–1200° F., say 1000° F. This support is then cooled to 32° F.–80° F., say about 72° F., and thereafter impregnated with desired alkaline earth metal.

In practice of the preferred embodiment 100 parts of, e.g., gamma alumina may be immersed in 10–300 parts, say 73 parts, of aqueous solution containing 0.15–10.0 parts, say 0.45 parts, of alkaline earth metal. This may correspond, for example, to 0.6–40 parts, say 1.8 parts, of calcium acetate; or to 0.21–14 parts, say 0.63 parts, of calcium oxide (as a suspension).

The gamma alumina is allowed to remain in contact with the aqueous solution at 50° F.–160° F., say 78° F., for 0.5–24 hours, say 1 hour. If desired, impregnation may be effected by use of a portion of the aqueous solution which is allowed to contact the alumina for 0.25–24 hours, say 1 hour. This portion of solution may then be poured off and replaced by a second portion which is allowed to contact the alumina for 0.25–24 hours, say 1 hour.

The alumina, now bearing the activating amount of alkaline earth metal (plus catalytically acceptable anion) distributed over the outside of the alumina and preferably throughout substantially the entire body of alumina, is then dried at 200° F.–500° F., say 300° F., for 0.25–24 hours, say 1 hour. The so-dried alumina is preferably then calcined at 700° F.–1400° F., say 1000° F., for 0.25–24 hours, say 2 hours.

The so-prepared alumina may be a novel gamma alumina containing an activating amount (typically 100–5000 ppm, preferably 1000–2500 ppm, say 2000 ppm) of alkaline earth metal distributed over the outside of said gamma alumina and preferably throughout substantially the entire body of said gamma alumina—together with at least one catalytically acceptable anion.

It will be apparent to those skilled in the art that when, e.g., calcium is added in the form of calcium acetate, the catalytically acceptable anion may be considered to be acetate. In this instance, it is probable that during subsequent operations, e.g. calcination, the acetate may be decomposed and expelled during calcination; and thus the catalytically acceptable anion may alternatively be considered to be oxide or possibly aluminate. Similar considerations may prevail when the metal is added as calcium carbonate, barium carbonate, etc., wherein the carbonate, etc. may be decomposed, etc. under conditions of calcining to leave oxide or aluminate as the net catalytically acceptable anion.

It is particularly unexpected to find that calcined high-purity prior art aluminas typified by Catapal S-types or by others (prepared, e.g., by precipitation of high-purity aluminum hydroxide from, e.g., calcium-free solutions) may possess undesirable properties because they do not contain alkaline earth metal ion; it is particularly unexpected to find that prior art calcined high-purity aluminas may be modified to enhance their catalytic properties by the addition thereto of an alkaline earth metal.

Although catalyst compositions prepared by the process of this invention may be useful for transalkylation, disproportionation, or other reactions (depending upon the catalytic metals or components subsequently added and the conditions of reaction), it is found that particularly desirable results may be achieved when the so-prepared alumina is used in steam dealkylation. Accordingly, the preparation of a typical catalyst for steam demethylation of toluene will be used as the typical preferred catalyst for description.

The catalyst composition which may be employed in practice of the steam dealkylation process of this invention may comprise a catalyst support as described supra, and distributed thereon and therein oxides of (i) a Group VIII metal, (ii) preferably a Group VI B metal, and (iii) preferably a Group I A metal.

The group VIII metal may include iron Fe, cobalt Co, nickel Ni, ruthenium Ru, rhodium Rh, palladium Pd, osmium Os, iridium Ir, and platinum Pt. Preferably, the Group VIII metal may be nickel or cobalt; and in the most preferred embodiment it is nickel.

The Group VI B metal may be chromium Cr, molybdenum Mo, or tungsten W; and in the preferred embodiment it is chromium Cr.

The Group I A metal, an alkali metal, may be lithium Li, sodium Na, potassium K, rubidium Rb, or cesium Cs. In the preferred embodiment it is potassium K.

In typical practice of the process of this invention, the catalyst composition may contain the following components in the indicated parts by weight (expressed as oxide).

In this table and in the others which follow, the metals are expressed as parts by weight of oxide. Thus, Group VIII-19 parts, means that the composition contains Group VIII metal in amount sufficient to make 19 parts of the corresponding oxide, e.g. NiO or Fe$_2$O$_3$. The support is expressed as parts by weight of alumina. The alkaline earth metal is expressed as parts by weight, and it will be apparent that the corresponding anion (which is not included in the stated parts by weight of the alkaline earth metal) may be any compatible anion such as oxide, carbonate, nitrate, acetate, formate, hydroxide, bicarbonate, etc.

TABLE

| Component | Broad | Preferred | Typical |
|---|---|---|---|
| Group VIII | 0.5-40 | 5-20 | 19 |
| Group VI B | 0-40 | 10-38 | 15 |
| Group I A | 0-5 | 1-4 | 2 |
| Support | 15-99.5 | 46-84 | 68 |
| Alkaline Earth Metal | 0.025-0.5 | 0.1-0.4 | 0.2 |

The preferred catalyst may be that containing nickel-chromium-potassium-aluminum-calcium; and the catalyst composition may contain the following (expressed as noted supra):

TABLE

| Component | Broad | Preferred | Typical |
|---|---|---|---|
| Ni | 6-40 | 5-20 | 19 |
| Cr | 0-40 | 10-38 | 15 |
| K | 0-5 | 1-4 | 2 |
| Al$_2$O$_3$ | 15-95 | 46-84 | 68 |
| Ca | 0.025-0.5 | 0.1-0.4 | 0.2 |

In terms of molar proportions, the catalyst may be represented by the formula:

$$a(VIII)_{2/n}O \cdot b(VI)_{2/m}O \cdot c(I)_2O \cdot dAl_2O_3 \cdot e(II)$$

wherein (VIII) represents a metal of Group VIII of the Periodic Table having a valence n, (VI) represents a metal of Group VI B of the Periodic Table of valence m, (I) represents a metal of Group I A of the Periodic Table, and (II) represents a metal of Group II A of the Periodic Table a may be 0.002-0.75, preferably 0.002-0.38, say 0.25; b may be 0-0.78, preferably 0.13-0.75, say 0.29; c may be 0-0.05, preferably 0.01-0.04, say 0.02; d is 0.15-0.995, preferably 0.46-0.84, say 0.68; and e is $6.25 \times 10^{-4} - 1.25 \times 10^{-2}$, preferably $2.5 \times 10^{-3} - 1 \times 10^{-2}$, say $3.6 \times 10^{-3}$.

In a preferred embodiment, the catalyst may be represented by the formula:

$$aNiO \cdot bCr_{2/3}O \cdot cK_2O \cdot cAl_2O_3 \cdot eCa$$

wherein a is 0.08-0.54, preferably 0.08-0.27, say 0.2; b is 0-0.78, preferably 0.21-0.75, say 0.29; c is 0-0.05, preferably 0.01-0.04, say 0.02; d is 0.15-0.95, preferably 0.46-0.87, say 0.68; and e is $6.25 \times 10^{-4} - 1.25 \times 10^{-2}$, preferably $2.5 \times 10^{-3} - 1 \times 10^{-2}$, say $3.6 \times 10^{-3}$.

In practice of one aspect of this invention, the catalyst may be prepared by immersing the charge calcined high-purity support containing, e.g., calcium in a solution containing the metal ions.

The support (242 parts), preferably containing alkaline earth metal ions, is cooled to 32° F.-80° F., say about 72° F., and wetted with 200-500 parts, say 250 parts, of solution prepared by dissolving soluble decomposable salts of metals of Group VI B and Group I A in aqueous solution; 0-1000 parts, preferably 500-1000 parts, say 792 parts, of salt of Group VI B metal, typically chromium nitrate nonahydrate, Cr (NO$_3$)$_3$·9H$_2$O, and 0-25 parts, preferably 10-20 parts, say 17.2 parts, of salt of Group I A metal, typically potassium nitrate, are dissolved in 50-500 parts, say 80 parts, of water to yield total solution in amount of 20-2525 parts, say 890 parts. (Although nitrates of the metals are preferably employed, acetates, formates, citrates, or other soluble decomposable salts may be used.)

The support, preferably containing alkaline earth metal ions, is permitted to stand for 0.5-30 hours, say 10 hours, and the solution (0-1000 parts, typically 460 parts) is decanted. The impregnated support is dried at 212° F.-400° F., say 300° F., then heated to decomposition temperature of typically 650° F.-1000° F., say 700° F., and calcined for 1-10 hours, say 2 hours, at 700° F.-1400° F., say 1000° F. This procedure is preferably repeated 2-4, preferably 2, times more until all the metal salt solution is absorbed by the support. The final pre-catalyst so prepared in amount of 242-1500 parts, say 383 parts, may be characterized by the formula:

$$b(VI)_{2/m}O \cdot c(I)_2O \cdot dAl_2O_3 \cdot e(II)$$

wherein (VI) represents a metal of Group VI B of the Periodic Table having a valence m, (I) represents a metal of Group I A of the Periodic Table, (II) represents a metal of Group II of the Periodic Table; b is 0-0.78, preferably 0.13-0.75, say 0.74; c is 0-0.05, preferably 0.01-0.04, say 0.02; d is 0.15-0.95, preferably 0.38-0.84, say 0.59; and e is $6.25 \times 10^{-4} - 1.25 \times 10^{-2}$, preferably $2.5 \times 10^{-3} - 1 \times 10^{-2}$, say $3.6 \times 10^{-3}$.

In the preferred embodiment, the composition of pre-catalyst may be:

$$bCr_{2/3}O \cdot cK_2O \cdot dAl_2O_3 \cdot eCa$$

wherein b is 0.25, c is 0.02, d is 0.59, and e is $2.5-5 \times 10^{-3}$ 242-1500 parts, say 383 parts, of pre-catalyst may be cooled to 32° F.-80° F., say 72° F., and impregnated with a decomposable salt of a Group VIII metal. Preferably, the solution may contain 50-700 parts, say 250 parts, of Ni(NO$_3$)$_2$·6H$_2$O in 50-700 parts, say 263 parts, of water. After 0.5-30 hours, say 10 hours, the excess nonabsorbed solution is decanted and the solids dried for 2-4 hours, say 2 hours, at 212° F.-400° F., say 300° F. The dried solid is reimpregnated with the remaining salt solution for 0.5-30 hours, say 10 hours, and dried again for 2-4 hours, say 2 hours, at 212° F.-400° F., say 300° F. Further treatment includes heating for 0.5-30 hours, say 1 hour, at 650° F.-1000° F., say 700° F., in flowing air to decompose the decomposable salts, typically nitrates, and calcining for 1-10 hours, say 2 hours, at 600° F.-900° F., say 700° F., to yield 260-1850 parts, say 462 parts, having a density of 0.7-1.5, say 1.11.

A product catalyst so prepared may be characterized by the formula:

$$a(VIII)_{2/n}O \cdot b(VI)_{2/3}O \cdot c(I)_2O \cdot dAl_2O_3 \cdot e(II)$$

wherein all the symbols are as noted supra except that a is 0.002-0.75, preferably 0.002-0.38, say 0.2; (VIII) represents a metal of valence n of Group VIII of the Periodic Table, preferably nickel; and Al$_2$O$_3$ represents the alumina support, preferably gamma alumina.

Preferred catalyst compositions may have the formulae:

$0.25NiO.0.27Cr_{\frac{2}{3}}O.0.02K_2O.0.64Al_2O_3.2.8\times 10^{-3}CaO$ $0.18NiO.0.54Cr_{\frac{2}{3}}O.0.02K_2O.0.51Al_2O_3.2.8\times 10^{-3}CaO$ $0.2CoO.0.2Cr_{\frac{2}{3}}O.0.02Na_2O.0.40Al_2O_3.2\times 10^{-3}MgO$ Expressed on a weight basis, the catalyst may have the composition set forth in the following table:

TABLE

| Component | Broad | Preferred | Typical |
|---|---|---|---|
| $(VIII)_{\frac{2}{n}}O$ | 0.5–40 | 5–20 | 17.7 |
| $(VI)_{2/3}O$ | 0–40 | 10–30 | 13.2 |
| $(I)_2O$ | 0–5 | 1–4 | 1.9 |
| $(Al_2O_3)$ | 15–99.5 | 46–84 | 61.6 |
| $(II)$ | 0.025–0.5 | 0.1–0.4 | 0.2 |

A preferred composition may contain 18.7% NiO, 14% $Cr_{\frac{2}{3}}O$, 2% $K_2O$, 65.3% $Al_2O_3$, and 0.28% CaO. Another preferred composition may contain 19.9% NiO, 15.2% $Cr_{\frac{2}{3}}O$, 2.1% $K_2O$, 60.5% gamma alumina, and 0.25% CaO.

The catalyst composition of this invention may be prepared by impregnating the alumina support with solutions of metal of Groups VIII, VI B, and/or I A. Typically, for example, it may be found that the catalyst may be prepared by:

(a) impregnating the support with a single solution containing all the metals, drying, and calcining;

(b) impregnating the support sequentially with the several solutions each containing one or more of the metals and thereafter drying and calcining;

(c) impregnating the support with one or more solutions containing less than all of the metals (i.e. species or amount), drying and/or calcining, thereafter impregnating the support with the remaining metals, and drying and/or calcining; etc.

It is unexpectedly found, however, that substantially superior results are achieved (in terms of conversion, yield, and/or selectivity) if the Group VI B and I A metals are dried and calcined on the catalyst support prior to the impregnation thereof with the Group VIII metal.

In the preferred embodiment, the catalyst support may thus be prepared by impregnating the support, typically a calcined high-purity alumina bearing an activating amount of an alkaline earth metal, with one solution containing soluble decomposable salts of the Group VI B and Group I A metals, typically chromium and potassium, drying and calcining, thereafter impregnating the so-obtained pre-catalyst with a solution of a soluble decomposable salt of the Group VIII metal, typically nickel, and drying and calcining.

The alkaline earth metal content of the alumina, or the alumina-derived catalyst, may be added to the calcined high-purity alumina ab initio or at any desired stage during processing. For example, the calcium content could be added at any stage in the interconversion of alpha monohydrate, alpha trihydrate, or beta trihydrate to gamma alumina. It may be added during further treating, i.e. before or during or as an integral step in addition of other components—e.g., as by addition of calcium sulfate, etc. The sole requirement is that the high-purity alumina be calcined at least once immediately prior to addtion of the alkaline earth metal composition.

In the preferred embodiment, the catalyst composition may be in the form of pellets, cylinders or randomly shaped particles; a typical catalyst composition may be in the form of cylinders, of diameter equal to height, of 10 mm.

It is a feature of the preferred catalyst of this invention that it be activated prior to use (e.g. in steam dealkylation). Preferably, activation may be carried out in the process which comprises:

(a) maintaining the unactivated catalyst in a hydrogen atmosphere at 750° F.–1400° F. for 0–30 hours, thereby forming a hydrogen-treated catalyst;

(b) maintaining the hydrogen-treated catalyst in steam-hydrogen atmosphere at 750°F.–1400° F. for 2–10 hours, thereby forming a steamed hydrogen-treated catalyst; and (c) cooling the steamed hydrogen-treated catalyst to 650° F.–900° F. in a steam or steam-hydrogen atmosphere, thereby forming an activated catalyst.

Activation of the steam dealkylation catalyst of this invention may preferably be carried out after the catalyst is in place in the reaction vessel. The vessel may be filled with catalyst composition to a bed bulk density of 50–80 pcf, say 70 pcf. In the first portion of the activation operation, the catalyst composition is heated to 750° F.–1400° F., preferably 900° F.–1100° F., say 1100° F., in the presence of inert gas containing at least about 30 mole % hydrogen. The inert gas will preferably be substantially free of active components which are capable of reacting with any of the materials in the system. It is particularly desirable that the gas be free of oxidizing components, including oxygen.

The gas may contain helium or, more preferably, light paraffins such as methane, ethane, propane, etc. Hydrogen may be present typically in amount of 30 mole %–100 mole %, preferably 80 mole %–100 mole %, say 100 mole %—i.e. the preferred embodiment may be that in which the gas consists essentially of hydrogen.

Preferably the catalyst composition may be maintained for 10–30 hours, typically 14–16 hours, say 15 hours, in a stream of flowing hydrogen typically flowing at a space velocity VHSV greater than about 3, more preferably greater than 100, say 100–500, typically 300 (at STP).

When activation is carried out at atmospheric pressure, as in the preferred embodiment, the partial pressure of hydrogen may be at least about 9 psia (400 mm Hg), preferably 12–15 psia, say 15 psia (760 mm Hg).

In the preferred second portion of the activation cycle, the hydrogen-treated catalyst may be maintained at 750° F.–1400° F., preferably 900° F.–1100° F., say 1100° F. (most preferably at about the same temperature as that employed in the first portion) in a flowing stream of hydrogen and steam. This stream may contain 15–50 mole %, preferably 20–40 mole %, say 30 mole %, of hydrogen; 50–80 mole %, preferably 60–80 mole %, say 70 mole %, of steam; and 0–10 mole %, preferably 0–5 mole %, say about 0 mole %, of inert gas such as helium, nitrogen, or light paraffins. Preferably, the gas may consist essentially of hydrogen and steam in molar ratio of 0.2–1, typically 0.25–0.5.

When activation is carried out at atmospheric pressure, as in the preferred embodiment, the partial pressure of hydrogen may be 100–380 mm Hg, preferably 150–300 mm Hg, say 240 mm Hg, and the partial pressure of steam may be 380–660, preferably 460–610, say 520 mm Hg.

The second portion of the activation procedure may be carried out for 2–10 hours, preferably 2–5 hours, say 2 hours, in a stream of flowing gas at a space velocity VHSV greater than about 1.5, preferably greater than 50, say 50–250, typically 150 (at STP).

Post-activation cooling is typically carried out by maintaining the activated catalyst in a stream of flowing stream for 1–13 hours, preferably 1–5 hours, say 2 hours, as the temperature is lowered to the steam dealkylation temperature of 600° F.–900° F., preferably 650° F.–900° F., say 800° F. Preferably, the steam is present during post-activation in amount of 50–100 mole %, typically 80–100 mole %, say about 100 mole %, of the flowing stream.

Steam dealkylation of the hydrocarbon charge may be carried out at steam dealkylating conditions by passing the charge at 600° F.–950° F., preferably 650° F.–900° F., say 800° F., and pressure of 0–400 psig, preferably 0–200 psig, say 0 psig, together with steam in amount of 2–25 moles, preferably 5–15 moles, say 6 moles, per mole of hydrocarbon charge (corresponding to 100–1250%, preferably 250–750%, say 300%, of the stoichiometric quantity) to a reaction zone. In commercial practice, it may be desirable to operate at, e.g., 125 psig.

During steam dealkylation at these conditions, alkyl groups are removed from the charge alkylaromatic hydrocarbons to form product hydrocarbons bearing lesser numbers of alkyl groups on the aromatic nuclei. When the charge hydrocarbon contains ethylbenzenes, for example, the product stream may contain dealkylated products including benzene. When the charge hydrocarbon contains xylenes, the product stream may contain toluene, benzene, etc. When the charge hydrocarbon stream contains toluene, as in the preferred embodiment, the product hydrocarbon stream may contain the paraffin derived from the charge, e.g. ethane or methane; and it may contain unreacted charge hydrocarbons in addition to other by-products.

Product hydrocarbon may be withdrawn from the reaction vessel and condensed. The liquid condensate may represent a recovery of 52–94 mole %, preferably 70–94 mole %, say 85 mole %, of the hydrocarbon charged.

In the case of a pure toluene charge, for example, the product (per 100 moles of charge toluene) may contain, on a mole basis, the following:

TABLE

| Component | Broad | Preferred | Typical |
|---|---|---|---|
| Unreacted Toluene | 4–79 | 13–70 | 37 |
| Benzene | 20–61 | 30–60 | 55 |
| Hydrogen | 20–183 | 90–180 | 165 |
| Carbon Dioxide | 20–61 | 30–60 | 55 |

In practice of the process of this invention according to one embodiment, the reaction is carried out on a short cycle basis; i.e. the reaction proper (with a charge of steam and hydrocarbon) is carried out for 0.5–2.5 minutes, preferably 0.5–2 minutes, say 1 minute, and then the catalyst is regenerated by shutting off the flow of hydrocarbon for 1–7.5 minutes, preferably 1.5–6 minutes, say 3 minutes. The ratio of regeneration time to reaction time may be 1–5, preferably 2–4, say 3.

It is found during practice of the process of this invention that it is possible to achieve improved catalyst activity. For example, the toluene conversion (in terms of mole percent of toluene charge converted) may be 50–95%, typically 85–95%, say 90%, in the preferred embodiment, in contrast to comparable processes wherein the corresponding values are less than 45%.

It is also a feature of the process of this invention in its preferred embodiment tht it permits attainment of benzene yield (in terms of mole percent of the charge toluene converted to benzene) which may be 40–60%, typically 50–55%, say 54%. Comparable processes may achieve benzene yields of less than about 35% and commonly 10–20%.

It is a particularly unexpected aspect of this invention that addition of an activating amount of alkaline earth metal to a calcined high-purity alumina in accordance with practice of this invention permits attainment of desirably high catalytic activity (e.g. high conversion, yield, ans selectivity in the case of steam dealkylation). This is in contrast to prior art aluminas which are not found to be satisfactory catalysts when calcium is added to a precalcined alumina base by impregnation (see, e.g., U.S. Pat. No. 3,846,287, column 2, lines 43–48).

It is also a feature of this invention, according to certain of its aspects, that it is possible to reproducibly test charge aluminas to determine which may benefit by the process of this invention by a Standard Hydration Test.

If the charge alumina as received is not a calcined alumina, calcination is effected prior to testing by maintaining at 700° F.–1200° F., say 850° F., for 10–24 hours, say 12 hours, in a stream of flowing air.

In accordance with certain of its aspects, this invention is directed to a method of testing the charge calcined alumina to determine its suitability for use in a hydrocarbon conversion process, and in particular its ability to effect hydrocarbon conversion to desired products without substantial formation of less desired products, which comprises:

(i) mixing said charge calcined alumina with an excess of water (preferably 10–50 parts of water per part of alumina), thereby forming an aqueous mixture;

(ii) heating said aqueous mixture (preferably to boiling);

(iii) digesting said heated aqueous mixture (preferably at 70° C.–80° C. for about an hour), during which operation the aqueous mixture becomes opaque in accordance with the formation, by rehydration, of beta alumina trihydrate which latter is observed as suspended material while the nonsuspended material is observed as a layer in the lower portion of the aqueous mixture; and (iv) determining the opacity of the upper portion of the aqueous mixture including the suspended material—a high opacity signifying unsuitability of the charge calcined alumina for use in steam dealkylation in which hydrocarbon conversion is effected to form desired product without substantial formation of less desired products (but sutitability for use in eg catalytic reforming), and a low opacity signifying a lesser degree of suitability.

In a preferred embodiment, an aliquot of the alumina is tested as follows:

(i) the aliquot is heated to 850° F. and maintained at this calcination temperature level for several hours, typically 4 hours;

(ii) the so-calcined alumina is pulverized or powdered in a pulverizing mill to yield powder which passes through a 325 mesh screen;

(iii) one gram of this finely-divided calcined alumina is added to 20 ml of boiling distilled water (in a test tube of diameter 18 mm and length 15 mm), the mixture agitated, and then digested for one hour at 70° C.–80° C. in a water bath; and (iv) after one hour, the test tube is inspected visually and the turbidity is recorded as:

clear—no material in suspension;

slight haze—liquid is transparent with only the slightest amount of turbidity apparent;

hazy—liquid is transparent with noticeable amount of turbidity;

cloudy—liquid is opaque and of white color.

It will be apparent that intermediate readings may be observed; and that the measuring procedure may be quantified by the use of, e.g., photometers which actually determine transmittance, etc. It is found, however, that the results are readily determinable and are reproducible; and, more importantly, they correlate with the desired information as will be observed infra.

Examination of the suspended material (by X-ray) reveals that it is beta alumina trihydrate.

As the calcined alumina remains in contact with the water during the test period, rehydration (to a varying degree, depending upon the nature of the charge calcined alumina) of at least a portion of the alumina occurs to beta alumina trihydrate. This latter is observed as a suspended material in the water; the nonsuspended alumina is observed as a layer at the bottom of the vessel.

When this test is carried out, the supernatant liquid may become less trasparent and more opaque than before in accordance with the degree of rehydration to the beta alumina trihydrate.

The aluminas which may be benefitted by the process of this invention includes those which, when subjected to this test, give a reading of cloudy or higher degrees of opacity, i.e. which readily rehydrate to substantial proportions of beta alumina trihydrate (and it appears that this correlates with the quantity of alkaline earth metal in the charge high-purity alumina, i.e. high rehydratability is found with low alkaline earth content and vice versa).

The charge high-purity aluminas which have a reading of "slight haze" may be benfitted to a lesser degree than those having a reading of "cloudy". Those having a reading of "clear" are benefitted least (if at all) by the process of this invention.

It appears that this test may be useful because it readily and simply measures the production of undesirable beta alumina trihydrate. When the catalyst is dried, this species is converted to eta alumina which provides an active surface on which cracking of product benzene occurs with formation of undesirable carbon deposits on the catalyst.

The presence of alkaline earth metals, on the high-purity charge alumina formulations of this invention, inhibits formation of beta alumina trihydrate, and its derivative materials, and thereby permits, e.g., steam dealkylation to be carried out with high recovery of desired product, e.g., benzene.

Thus, it is apparent that if a charge calcined alumina gives a reading of, e.g., cloudy it may be improved by addition thereto of small quantities of alkaline earth metals (preferably calcium or magnesium)—which inhibit the rehydration of alumina and thus permit attainment of desired high yields in reactions such as steam dealkylation.

Practice of the process of this invention may be apparent to those skilled in the art from the examples which follow, in which all parts are parts by weight unless otherwise specified.

DESCRIPTION OF PREFERRED EMBODIMENTS

EXAMPLES I–XI

In this series of comparative examples, various commercially-available high-purity alumina samples are tested by the above-noted "Standard Hydration Test". The alumina of Examples I–V represents samples taken from different containers of a commercially-available alumina sold under the designation American Cyanamid Aero-100 brand alumina. The alumina of Example VI is a sample of Catapal S-type alumina marketed by Conoco Inc. The samples of Examples VII–IX represent samples taken from different containers of a commercially-available alumina sold by Harshaw Chemical Company under the designation Catapal SB-type gamma alumina. The alumina of Example X is a sample of a commercially-available alumina sold by Norton Company under the designation LA-6173. The alumina of Example XI is a sample of a commercially-available alumina sold by Kaiser Chemicals Inc. under the designation KA-201. All the aluminas are in the form of 1/16-inch extrudates except (i) the sample of Example V is ⅛-inch extrudates, and (ii) the sample of Example XI is ⅛-inch spheres.

All of the aluminas were nominally "high-purity" gamma aluminas. Their properties, an determined, are set forth in the table which follows.

The table also includes analyses for silicon, iron, magnesium and titanium (all as parts per million of oxide), sulfur (in % sulfate), and a qualitative spectal analysis carried out in a Baird Associates 3-meter Grating Spectrograph.

In the spectral analysis, the metals are determined as present:

(i) in major quantities (abbreviated Mj), i.e. in amount of 10–100 parts.

(ii) in minor quantities (abbreviated Mn), i.e. in amount of 1–10 parts.

(iii) in high trace quantities (abbreviated HTr), i.e. in amount of 0.1–1 parts.

(iv) in trace quantities (abbreviated Tr), i.e. in amount of 0.01–0.1 parts.

(v) in weak trace quantities (abbreviated WTr), i.e. in amount of 0.001–0.01 parts.

(vi) in very weak trace quantities (abbreviated VWTr), i.e. in amount of 0.0001–0.001 parts.

In certain instances, the table includes values in parentheses; and these values are the values given by the supplier. All other values are as actually measured. The % sulfate is measured by The Leco High Temperature Combustion Method.

TABLE

| Example | Crush Strength lbs. pellet | Crush Strength lbs. inch | Apparent Bulk Den. g/cc | Surface Area m²/S | Abrasion Coeff. | N₂ Pore Volume ml/g | Si ppm | Fe ppm | Mg ppm | Ti ppm | % S | Qualitative Spectral Analysis |
|---|---|---|---|---|---|---|---|---|---|---|---|---|
| I | 9.3 | 53 | 0.67 | 258 | 0.35 | 0.740 | 1140 | 556 | 91 | 135 | 0.45 | MJ-AL |

TABLE-continued

| Example | Crush Strength lbs. pellet | Crush Strength lbs. inch | Apparent Bulk Den. g/cc | Surface Area m²/S | Abrasion Coeff. | N₂ Pore Volume ml/g | Si ppm | Fe ppm | Mg ppm | Ti ppm | % S | Qualitative Spectral Analysis |
|---|---|---|---|---|---|---|---|---|---|---|---|---|
| II | 10.4 | 55 | 0.63 | 224 | 0.11 | 0.715 | 6850 | 501 | 141 | 85 | 0.16 | Tr-Si WTr-Mg,Fe Mj-Al |
| III | 10.2 | 59 | 0.64 | 232 | 0.09 | 0.742 | 5200 | 410 | 513 | 196 | 0.15 | Tr-Mg,Si WTr-Fe VWTr-Ti,La,V HTr-Si Tr-Mg VWTr-Fe,Mo,Ca,Na |
| IV | 8.8 | 54 | 0.64 | 221 | 0.11 | 0.510 | 5410 | 343 | 592 | 134 | 0.20 | Tr-Si WTr-Mg VWTr-Fe,Ti |
| V | 12.5 | 57 | 0.65 | 215 | 0.02 | 0.686 | 2510 | 249 | 343 | 114 | 0.16 | Tr-Si WTr-Mg VWTr-Fe |

In addition to the reported values for Example XI, the alumina of that example contained 851 ppm Na₂0, less than 2 ppm CuO, and 9 ppm V.

In practice of certain aspects of this invention, the eleven aluminas of the table are tested by the Standard Rehydration Test Procedure of this invention, as disclosed supra, and found to give the following results:

| Example | Reading |
|---|---|
| I | Cloudy |
| II-V | Slight Haze |
| VI | Cloudy |
| VII-IX | Cloudy |
| X | Cloudy |
| XI | Cloudy |

Each of these eleven aluminas is tested to determine its activity in a typical catalytic process—steam dealkylation of toluene. This is carried out by preparing a standard catalyst and determining the activity of the catalyst in the standard reaction.

The standard catalyst is prepared by the following procedure:

Solution "A" containing 527 g. of chromium nitrate nonahydrate (Cr(NO₃)₃.9H₂O) and 28 g. of potassium nitrate (KNO₃) in 155 cc of distilled water was prepared. The support (383 g.) was wetted with 390 g. (approximately 55 wt. % of the total) of solution "A" and the mixture was stirred till all the liquid was adsorbed on the support. The material was then charged to a vycor tube and heated at 700° F. to decompose the nitrates. The recovered material (448 g.) was wetted with the remainder of solution "A" and the nitrates were decomposed at 700° F., and the material was then calcined in a muffle furnace at 1000° F. for 2 hours. 497 g. of pre-catalyst was recovered.

Solution "B" containing 502 g. of nickel nitrate hexahydrate (Ni(NO₃)₂.6H₂O) in 160 cc distilled water was prepared. The pre-catalyst (497 g.) was wetted with 364 g. of solution "B" and was stirred till all the solution was adsorbed. The nitrates were decomposed by heating at 700° F. and the decomposed material (597 g.) was wetted with the remainder of solution "B" and stirred till all the liquid was adsorbed. The nitrates were decomposed and the material was finally calcined in a muffle furnace at 700° F. for 2 hours. The finished catalyst (643 g.) was recovered and its analysis showed 20.0% NiO, 15.3% Cr₂O₃, 2.04% K₂O and the balance alumina.

Evaluation of the Catalysts

In each of the evaluation runs 100 cc (or 100 g. d≅1.0) of catalyst are loaded into a tubular reactor and are activated by passing H₂ (0.5 standard liters per minute) at 0-40 psig and 950° F.-1200° F. for 14-16 hours.

In each run the catalyst is activated prior to reacting by heating to 900° F. in the presence of flowing (1 liter per minute) hydrogen, holding at 900° F. for 14-16 hours in 0.5 liters per minute of hydrogen, and then holding at 900° F. for 2 hours in steam (35 ml water per hour) plus 0.5 liters per minute of hydrogen. At the end of this period, the hydrogen flow is turned off; and the reactor temperature is lowered to 800° F. and the reactor temperature is maintained in the presence of steam alone for 0.5 hours.

At this time, the flow of toluene is initiated. The average temperature in the bed of catalyst is maintained at 800° F.; the pressure at the input to the bed is maintained at 125 psig; the toluene WHSV (the weight hourly space velocity, based upon the volume of the empty reactor, at which the toluene is passed through the catalytic bed) is maintained at 0.4; the mole ratio of steam to toluene is maintained at 5.8.

The product is analyzed to determine:

(a) the toluene conversion, as mole percent of the toluene charge;

(b) the benzene yield, as mole percent of the toluene charge; and (c) the benzene selectivity, as mole percent of the toluene converted.

In Examples I-XI, it is found that the conversion, yield, and selectivity are essentially constant for the alumina provided by a particular supplier (except for one sample, Example I, of the Aero-100 brand of alumina which contained 91 ppm Mg and gave unsatisfactory results, i.e. low yield and selectively); and they average out as follows (including the results of Example I):

| Example | Toluene Conversion | Benzene Yield | Benzene Selectivity |
|---|---|---|---|
| I | low | low | low |
| II-V | 50 | 46 | 92 |
| VI | 47 | 31 | 67 |
| VII-IX | 54 | 27 | 50 |

-continued

| Example | Toluene Conversion | Benzene Yield | Benzene Selectivity |
|---|---|---|---|
| X | 46 | 26 | 56 |
| XI | 46 | 27 | 58 |

The data may be tabulated to reveal a startling result:

| Example | Mg ppm | Benzene Selectively |
|---|---|---|
| I* | 91 | low i.e. below 20 |
| II | 141 | 88 |
| III | 513 | 91 |
| IV | 592 | 87 |
| V | 343 | 87 |
| VI* | 16 | 58 |
| VII* | 14 | 52 |
| VIII* | 65 | 45 |
| IX* | 55 | 61 |
| X* | 22 | 56 |
| XI* | 56 est | 64 |

It is generally believed that in steam dealkylation, benzene selectivity must be at least about 85% for the process to be economically satisfactory.

Results comparable to those noted are achieved when the alkaline earth metal is calcium, barium, strontium, etc., as well as magnesium.

EXAMPLE XII

In practice of the process of this invention, the alumina employed is the Catapal S-type alumina of Example VII. The gamma alumina support (200 g.) is treated with 1.28 g. $CaSO_4$ in 144 cc of 5% aqueous $HNO_3$ solution. The treated alumina is dried and then calcined in a muffle furnace at 1000° F. for one hour.

The catalyst is prepared on 154 g. of $CaSO_4$ treated support using 263.3 g. of solution "A" (containing 212 g. $Cr(NO_3)_3.9H_2O$ and 11.3 g. $KNO_3$ in 40 cc distilled water) and 238 g. of solution "B" (containing 198 g. $Nl(NO_3)_2.6H_2O$ in 40 cc distilled water) by following the standard procedure described for Examples I-XI above.

255 g. of finished catalyst with nominal composition 19% NiO, 15% $Cr_2O_3$, 2% $K_2O$, 0.45% $SO_4$ (i.e. $CaSO_4$ in amount sufficient to yield 0.45% sulfate iron) and 0.19% Ca (1900 ppm) on alumina is recovered.

EXAMPLE XIII 200 g. of the support of Example VIII is treated with a solution containing 1.25 g. calcium formate in 144 cc distilled water. The treated support is dried and then calcined at 1000° F. for one hour.

The catalyst is prepared on 154 g. of calcium formate treated alumina using solutions "A" and "B" described in Example XII by following the standard procedure described in Examples I-XI.

258 g. of finished catalst having nominal composition 19% NiO, 15% $Cr_2O_3$, 2% $K_2O$ and 0.12% Ca as calcium oxide is recovered the Ca having been placed on the alumina prior to addition of Ni and Cr.

The catalysts of experimental Examples XII-XIII are evaluated by the Standard Evaluation described supra. Details of the evaluation are set forth in the following table which also includes the results of Example I*. All of these catalysts are prepared in comparable manner except that the control catalyst of Example I* has not been modified by addition of calcium.

The liquid hydrocarbon yield represents liquid condensed at the outlet of the catalyst bed. The analysis of the liquid hydrocarbon (based on area percent of the curve obtained by gas chromatograph) is shown.

TABLE

| Example No. | I* | XII | XIII |
|---|---|---|---|
| Catalyst | Untreated | $CaSO_4$ | Ca Formate |
| Run Conditions | | | |
| Average Bed Temp., ° F. | 798 | 810 | 810 |
| Pressure, psig | 125 | 125 | 125 |
| Toluene WHSV, g/hr/g Cat. | 0.41 | 0.41 | 0.41 |
| Steam/Toluene - mole ratio in feed | 5.79 | 5.91 | 6.34 |
| Performance Data | | | |
| Liquid Hydrocarbon Yield, wt. % toluene charge | 70.86 | 87.19 | 68.55 |
| Composition of Liquid Hydrocarbon Product | | | |
| GC Area % | | | |
| Unidentified Light Ends | 0.04 | 0.00 | 0.00 |
| Methyl cyclopentane | 0.00 | 0.01 | 0.00 |
| Cyclohexane | 0.05 | 0.27 | 0.00 |
| Methyl Cyclohexane | 0.00 | 0.10 | 0.00 |
| Benzene | 33.73 | 55.19 | 44.79 |
| Toluene | 63.85 | 44.27 | 53.55 |
| $C_8$ Aromatics | 2.34 | 0.16 | 1.65 |
| Toluene Conversion, mol % toluene charge | 53.63 | 61.31 | 63.29 |
| Benzene Yield, mol % toluene charge | 25.38 | 57.20 | 36.21 |
| Benzene Selectivity, mol % | 53.86 | 93.29 | 57.21 |

*Control Example

From the above table it will be apparent that the Experimental Examples XII-XIII give substantially better results than are attained in Control Example I when measured in terms of toluene conversion, benzene yield, and benzene selectivity. It may be seen that for each mole of toluene charge, for example, the product streams of Examples XII-XIII contain about 1.5-2+ times as much benzene as does the stream of Control Example I*. The benzene selectivity of Example XII of 93.29% (which contributes to the high overall yield) is particularly outstanding.

Results comparable to those shown in Example XII are achieved if the alkaline earth metal is as follows, present in the indicated activating amounts in parts per million based on the alumina:

| Example | Metal | ppm |
|---|---|---|
| XIV | Ca | 100 |
| XV | Ca | 550 |
| XVI | Ca | 3000 |
| XVII | Mg | 200 |
| XVIII | Mg | 800 |
| XIX | Mg | 1700 |
| XX | Mg | 4500 |
| XXI | Ba | 2000 |
| XXII | Ba | 150 |
| XXIII | Ba | 2400 |
| XXIV | Sr | 3500 |
| XXV | Sr | 2000 |
| XXVI | Sr | 250 |

Results comparable to those shown in Example XII are also obtained if one modifies (as by addition thereto of 2000 parts of calcium, from calcium sulfate) the otherwise inactive supports of the following examples:

| Example | Addition of 2000 ppm Ca to the support of Example: |
|---------|---|
| XXVII | T |
| XXVIII | VI |
| XXIX | VII |
| XXX | VIII |
| XXXI | IX |
| XXXII | X |
| XXXIII | XI |

In each case, it is found that substantially improved results are achieved. For example, illustrative improvements are as follows:

| Example | Toluene Conversion | Benzene Yield | Benzene Selectivity |
|---------|---|---|---|
| II-V | 50 | 46 | 92 |
| VII*-IX* (untreated) supra | 54 | 27 | 50 |
| XXIX-XXXI (aver) treated | 60 | 57 | 94 |

From the above table it is apparent that the results of Examples XXIX-XXXI show that it is possible to improve (by the process of this invention) the inactive alumina of Examples VII*-IX* to a substantial degree. The improved products of Examples XXIX-XXXI are outstandingly superior to the control of Examples VII--IX; and it is unexpected that one should be almost able to double the yield and selectivity of the untreated alumina by the process of this invention.

It is also found that the novel treated aluminas of this invention may be used as support for otherwise standard catalysts in a wide variety of reactions. Typical of these are reforming, cracking, disproportionation, etc.

Improved results are achieved when these reactions are carried out in the presence of prior art calcined catalysts which are different in that the support on which they are prepared is a high-purity, inactive alumina which has been activated by the process of this invention.

It will be apparent to those skilled in the art that the novel technique of this invention gives to the processor and/or the catalyst manufacturer a tool which readily permits one to activate high-purity calcined aluminas which have heretofore been unexpectedly found to be inactive when used in catalyst systems. It is particularly unexpected that the addition to these high-purity calcined aluminas of an alkaline earth metal in amounts as small as, e.g., 100-500 ppm should be effective—because in many of the reactions in which these systems are employed alkaline earth metals are believed to be of little or no value as catalysts, especially at the low levels at which they may be added in practice of this invention (which levels are below the levels normally used as catalysts in the indicated reaction).

It appears that the technique of this invention may be effective because alkaline earth metals, preferably calcium or magnesium (and preferably in non-halide systems), when calcined onto the surface of, e.g., catapal-type aluminas, desirably inhibit the rehydration of the gamma alumina to beta alumina trihydrate. It is this latter (when dried on the impregnated surface of the alumina mass and there converted to eta alumina of high cracking quality) which controls the activity of the catalyst. The finding of this invention appears to be predicated at least in part on the fact that the presence of small amounts of alkaline earth metals inhibits the noted rehydration and thus permits one to moderate the cracking activity to a point at which it permits less severe reactions (such as dealkylation, etc.) to proceed.

Although this invention has been illustrated by reference to specific embodiments, it will be apparent to those skilled in the art that various changes and modifications may be made which clearly fall within the scope of this invention.

What is claimed is:

1. The method of testing a charge calcined alumina to determine its suitability for use in a hydrocarbon conversion process including steam dealkylation, and in particular its ability to effect hydrocarbon conversion to desired products without substantial formation of less desired products, which comprises:
   (i) mixing said charge calcined alumina with an excess of water, thereby forming an aqueous mixture;
   (ii) heating said aqueous mixture;
   (iii) digesting said heated aqueous mixture during which opertion the aqueous mixture becomes opaque in accordance with the formation, by rehydration, of beta alumina trihydrate, which latter is observed as suspended material while the nonsuspended material is observed as a layer in the lower portion of the aqueous mixture; and
   (iv) determining the opacity of the upper portion of the aqueous mixture including the suspended material—a high opacity signifying unsuitability of the charge calcined alumina for use in steam dealkylation in which hydrocarbon conversion is effected to form desired products without substantial formation of less desired products, and a low opacity signifying a higher degree of suitability.

2. The method of testing a charge calcined alumina to determine its suitability for use in steam dealkylation of hydrocarbons which comprises:
   (i) mixing one part of said charge calcined alumina with 10-50 parts of water, thereby forming an aqueous mixture;
   (ii) heating said aqueous mixture to boiling;
   (iii) digesting said heated aqueous mixture at 70°-80° C. during which operation the aqueous mixture becomes opaque in accordance with the formation, by rehydration, of beta alumina trihydrate, which latter is observed as suspended material which the nonsuspended material is observed as a layer in the lower portion of the aqueous mixture; and
   (iv) determining the opacity of the upper portion of the aqueous mixture including the suspended material—a low opacity signifying suitability of the charge calcined alumina for use in steam dealkylation, and a high opacity signifying a lesser degree of suitability for use in steam dealkylation.

* * * * *